United States Patent [19]

Breitenbach et al.

[11] Patent Number: 6,063,821

[45] Date of Patent: *May 16, 2000

[54] TRANSPARENT RAPID RELEASE COMPOSITIONS OF NON-STEROIDAL ANALGESICS

[75] Inventors: Jörg Breitenbach, Mannheim; Axel Sanner, Frankenthal; Joerg Rosenberg, Ellerstadt, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/913,509

[22] PCT Filed: Mar. 9, 1996

[86] PCT No.: PCT/EP96/01021

§ 371 Date: Sep. 16, 1997

§ 102(e) Date: Sep. 16, 1997

[87] PCT Pub. No.: WO96/29053

PCT Pub. Date: Sep. 26, 1996

[30] Foreign Application Priority Data

Mar. 21, 1995 [DE] Germany ............ 195 09 805

[51] Int. Cl.⁷ .................................. A61K 31/79

[52] U.S. Cl. ......................... 514/772.5; 424/486

[58] Field of Search ................... 424/486; 514/772.5

[56] References Cited

U.S. PATENT DOCUMENTS

| | | | |
|---|---|---|---|
| 4,801,460 | 1/1989 | Goertz et al. | 424/465 |
| 5,631,296 | 5/1997 | Birrenbach et al. | 514/570 |
| 5,667,807 | 9/1997 | Hurner et al. | 424/489 |
| 5,741,519 | 4/1998 | Rosenberg et al. | 424/464 |

FOREIGN PATENT DOCUMENTS

| | | |
|---|---|---|
| 0358107 | 3/1990 | European Pat. Off. . |
| 0609983A2 | 8/1994 | European Pat. Off. . |

OTHER PUBLICATIONS

Abstract of DE 4138513 Nov. 1991.
Abstract of JP 4363332A T. Kagiwada et al. Dec. 1992.
Abstract of EP 94300210 Aug. 1994 Bock et al.
Abstract of DE 04138513A, Jul. 1994.

*Primary Examiner*—Peter F. Kulkosky
*Attorney, Agent, or Firm*—Keil & Weinkauf

[57] ABSTRACT

Transparent rapid release active substance compositions obtainable by extrusion of melts, containing non-steroidal analgesics, homopolymers of N-vinylpyrrolidone, saccharides or sugar alcohols and sodium or potassium salts.

14 Claims, No Drawings

TRANSPARENT RAPID RELEASE COMPOSITIONS OF NON-STEROIDAL ANALGESICS

The present invention relates to transparent rapid release compositions of non-steroidal analgesics with antipyretic and antiinflammatory action, obtainable by extrusion of a melt comprising, besides one or more active substances, a) 50–100% by weight of homopolymers of N-vinylpyrrolidone with a Fikentscher K value of 30,
b) 0–30% by weight of water-soluble saccharides or sugar alcohols or mixtures thereof, and
c) 0–20% by weight of one or more physiologically acceptable salts of sodium or of potassium, where the stated amounts are based on the total of a), b) and c), and subsequent shaping.

The invention furthermore relates to a process for producing such compositions.

Rapid release of the active substance is of crucial importance particularly with analgesics in order to achieve a rapid onset of the pain-relieving action.

In the case of active substances with low solubility in water, as represented, for example, by the organic acids with analgesic activity, rapid release of sufficient doses is often not simple to achieve.

EP-A 607 467 proposes to promote rapid release of ibuprofen by adding basic salts which are applied during the pelleting process in the form of aqueous solutions to the active substance which has previously been mixed with an ancillary substance. The pellets are subsequently compressed to tablets in a conventional way. However, this procedure is relatively elaborate and therefore rather unfavorable economically.

It is furthermore known that drug forms can be produced in a very economic manner by extrusion of polymer melts which contain active substances, with subsequent continuous shaping.

EP-B 240 904 describes such a process for producing solid pharmaceutical forms by extrusion of polymer melts which contain active substances, using as polymers homo- or copolymers of N-vinylpyrrolidone.

However, a fundamental problem in the process of this type is that the matrix-forming polymers on the one hand are sufficiently melt-processable, or become processable by addition of a plasticizing substance, at the processing temperatures but, on the other hand, lead to stable drug forms under the usual storage conditions, with which no cold flow occurs.

This problem is all the more difficult to solve when the intention is to produce rapid release drug forms. Normally suitable for this purpose are, in particular, relatively low molecular weight polymers which rapidly dissolve in the digestive juices. However, it is precisely these which show the phenomenon of cold flow of the finished drug forms to a pronounced extent. High molecular weight polymers do not usually show rapid release and can scarcely be extruded without plasticizers because the glass transition temperature (DIN 52324) is considerably higher.

An additional problem arises when the intention is to produce transparent drug forms by melt extrusion. The active substance is completely uniformly distributed without compartmentalization only in transparent forms. This is indispensable for rapid release. In addition, the use of transparent forms simplifies quality control and patient compliance.

It is an object of the present invention to find transparent rapid release compositions of non-steroidal analgesics which can be produced in a simple manner by melt extrusion with subsequent shaping and have good storage stability.

We have found that this object is achieved by the compositions defined at the outset.

Suitable active substances according to the invention are non-steroidal analgesics with antipyretic and antiinflammatory effect, as also used for symptomatic antirheumatic therapy.

Suitable active substances are, accordingly, derivatives of salicylic acid such as acetylsalicylic acid and derivatives of other organic acids and pyrazole derivatives. Thus, suitable active substances are aryl acid derivatives such as diclofenac, tolmetin or zomepirac, also arylpropyl acid derivatives such as ibuprofen, naproxen, fenoprofen, flurbiprofen or ketoprofen, or else indole- and indeneacetic acid derivatives such as indometacin or sulindac. Examples of suitable pyrazole derivatives are for example phenazone, aminophenazone, metamizole, propyphenazone, phenylbutazone or oxyphenbutazone.

Preferred active substances are ibuprofen, acetylsalicylic acid and ketoprofen, sulindac, indometacin, flurbiprofen.

It is also possible to use mixtures of active substances.

The compositions according to the invention contain as component a) a homopolymer of N-vinylpyrrolidone with a Fikentscher K value of 30 (for the definition of the K value see "H. Fikentscher, Cellulose-Chemie" 13 (1932), 58–64 and 71–74). This homopolymer is readily soluble in water, where "soluble in water" means that at least 0.5 g, preferably at least 2 g, of the polymer dissolves in 100 g of water at 20° C., where appropriate as colloidal solution. The preparation of the homopolymer is generally known.

Suitable as components b) are water-soluble saccharides or sugar alcohols or mixtures thereof. Suitable saccharides are, in particular, mono- or disaccharides such as galactose, fructose, dextrose, mannose, maltose, isomaltulose (palatinose), lactose or sucrose.

Examples of suitable sugar alcohols are mannitol, xylitol, sorbitol, adonitol, dulcitol and generally pentitols and hexitols.

Suitable as components c) are physiologically tolerated sodium and/or potassium salts, for example sodium acetate, potassium acetate, sodium carbonate, potassium carbonate, sodium bicarbonate, sodium hydroxide, potassium hydroxide, sodium chloride or potassium chloride, with sodium acetate being preferred.

The ratios of the amounts of components a), b) and c) are chosen according to the invention so that the compositions comprise a) 50–100% by weight, preferably 60–90% by weight, of component a),
b) 0–30% by weight, prefearbly 5–20% by weight, of component b), and
c) 0–20% by weight, preferably 5–20% by weight, of component c), where the stated amounts are based on the total of a), b) and c).

Preferred compositions contain 80–95% by weight of component a) and 5–20% by weight of component c), based on the total of a) and c).

The total content of active substance in the compositions may vary within wide limits depending on the dose required and the release rate. Thus, the content of active substance can be from 0.1 to 90, preferably 0.5 to 60, % by weight of the complete composition.

The compositions according to the invention may additionally contain conventional pharmaceutical ancillary substances and in the usual amounts.

The mixing of the active substance or active substances with the polymeric binders and, where appropriate, pharmaceutical additives can take place before or after the melting of the polymeric binder by processes customary in the art. The mixing is preferably carried out in an extruder, preferably a twin screw extruder or a single screw extruder with mixing compartment.

The melts are solvent-free. This means that no water and no organic solvent is added.

Production takes place by extrusion at 50–180° C., preferably 60–150° C., and subsequent shaping of the still plastic extrudate, eg. by shaping to tablets, for example as described in EP-A 240 906 by passing the extrudate between two rolls which are driven in opposite directions and have mutually opposite depressions in the casing, whose design determines the shape of the tablets. Cold cutting is also suitable.

The hot-cut method is preferred. This entails the extrudates being pelletized immediately after emergence from the die arrangement on the extruder, for example by rotating knives or another suitable arrangement, expediently to pellets whose length is about the same as the diameter of the extrudate. These cut-off pellets are cooled in the stream of air or gas to such an extent that the surface is tack-free even before contact with other pellets or a vessel wall but, on the other hand, the pellets are still sufficiently plastic that they acquire a spherical shape by impacts, for example with the wall of a subsequent cyclone. This results in a simple manner in pellets which are sustantially spherical or lentil-shaped and have diameters of from 0.5 to 4, preferably 0.8 to 2, mm. The preferred smaller particles are primarily suitable for filling capsules.

The solid drug forms can also be provided with a conventional coating to improve the appearance and/or the taste (sugar-coated tablet).

The compositions according to the invention of non-steroidal analgesics with antipyretic and antiinflammatory action are transparent, stable on storage and display rapid release. "Rapid release" means that the release of the active substance measured by the USP XXII paddle method after 30 min is at least 70%.

Surprisingly, despite the use of a relatively high molecular weight polymer, even drug forms with high weights, such as 1000 mg, showed rapid release. It is also advantageous that large tablets can be used as pastilles without being swallowed, and the addition of sugar alcohols also means that no taste problems occur. The swallowing of large tablets is often associated with difficulty in particular for elderly patients or patients with dysphagia, so that rapid release pastilles have great advantages.

EXAMPLES

The compositions indicated in each of the examples were premixed and introduced into the feed section of a twin screw extruder (Werner & Pfleiderer, ZSK 30). The melt extrusion took place with a product throughput of 3–4 kg/h. The temperatures in the individual zones ("sections") of the extruder, and the temperature of the heated die strip are stated for each of the tests. Bolus tablets weighing 1000 mg were produced from the extrudate by the calendering process described in EP-B 240 906.

The release of active substance was measured by the USP XXIII paddle method. This in vitro test method is used to determine the rate of dissolution of shaped articles containing active substances, eg. tablets.

This was done by equilibrating 900 ml of a phosphate buffer with a pH of 6.8, with addition of 0.1% sodium lauryl sulfate, in a 1 l round-bottom vessel at 37° C. An appropriate amount of the drug form was weighed in. The release of active substance from the boli was determined in this USP XXI no-change test at a paddle speed of 100 rpm after 30 min in each case by UV spectroscopy.

Example 1

Temperatures of the extruder zones (sections 1–5) 20, 80, 140, 130, 130° C., temperature of extruder head 130° C., temperature of die strip 130° C.

| Active substance | component a |
|---|---|
| Ibuprofen 20% by weight | polyvinylpyrrolidone K value 30, 80% by weight |

Release after 30 min 82%

Example 2

Temperatures of the extruder zones (sections 1–5) 60, 120, 120, 110, 120° C., temperature of extruder head 130° C., temperature of die strip 120° C.

| Active substance | component a | component b |
|---|---|---|
| Ibuprofen 20% by weight | polyvinylpyrrolidone K value 30, 70% by weight | D-mannitol 10% by weight |

Release after 30 min 72%

Example 3

Temperatures of the extruder zones (sections 1–5) 60, 120, 120, 120, 130° C., temperature of extruder head 130° C., temperature of die strip 160° C.

| Active substance | component a | component b |
|---|---|---|
| Ibuprofen 20% by weight | polyvinylpyrrolidone K value 30, 60% by weight | D-mannitol 20% by weight |

Release after 30 min 70%

Example 4

Temperatures of the extruder zones (sections 1–5) 70, 130, 130, 140, 130° C., temperature of extruder head 130° C., temperature of die strip 160° C.

| Active substance | component a | component c |
|---|---|---|
| Ibuprofen 20% by weight | polyvinylpyrrolidone K value 30, 66.5% by weight | Na acetate 13.5% by weight |

Release after 30 min 95%

Example 5

Temperatures of the extruder zones (sections 1–5) 70, 130, 130, 140, 130° C., temperature of extruder head 130° C., temperature of die strip 160° C.

| Active substance | component a | component c |
|---|---|---|
| Ibuprofen 20% by weight | polyvinylpyrrolidone K value 30, 75% by weight | Na acetate 5% by weight |

Release after 30 min 95%

Example 6

Temperatures of the extruder zones (sections 1–5) 60, 120, 120, 120, 130° C., temperature of extruder head 130° C., temperature of die strip 160° C.

| Active substance | component a | component b | component c |
|---|---|---|---|
| Ibuprofen 20% by weight | polyvinylpyrrolidone K value 30, 70% by weight | D-mannitol 5% by weight | Na acetate 5% by weight |

Release after 30 min 80%.

We claim:

1. A transparent rapid release preparation of a non-steroidal analgesic with antipyretic and antiinflammatory action, wherein the release of the analgesic measured by the USP XXII paddle method after 30 minutes is at least 70%, which is obtainable by extrusion of a melt comprising an effective amount of one or more non-steroidal analgesics with antipyretic and antiinflammatory action, and
   a) from 50 to 100% by weight of a homopolymer of N-vinylpyrrolidone having a Fikentscher K value of 30,
   b) from 0 to 30% by weight of a water-soluble saccharide or sugar alcohol, or a mixture thereof, and
   c) from 0 to 20% by weight of one or more physiologically acceptable salts of sodium or of potassium,
where the weight percentages are based on the total of a), b), and c), and subsequent shaping.

2. The preparation defined in claim 1, comprising from 5 to 20% by weight of component c).

3. The preparation defined in claim 1, wherein the non-steroidal analgesic is ibuprofen.

4. The preparation defined in claim 1, wherein component c) is sodium acetate.

5. A process for producing a transparent rapid release preparation as defined in claim 1, which comprises
   i) extruding a melt comprising one or more non-steroidal analgesics with antipyretic and antiinflammatory action, and
      a) from 50 to 100% by weight of a homopolymer of N-vinylpyrrolidone having a Fikentscher K value of 30,
      b) from 0 to 30% by weight of a water-soluble saccharide or sugar alcohol, or a mixture thereof, and
      c) from 0 to 20% by weight of one or more physiologically acceptable salts of sodium or of potassium,
   where the weight percentages are based on the total of a), b) and c), at from 50 to 180° C., and
   ii) subsequent shaping.

6. A transparent rapid release preparation, wherein the release of the analgesic measured by the USP XXII paddle method after 30 minutes is at least 70%, comprising
   i) an effective amount of at least one non-steroidal analgesic with antipyretic and antiinflammatory action, and
   ii) at least one homopolymer of N-vinylpyrrolidone having a Fikentscher K value of 30, said homopolymer being present in an amount of 50 to 100 per cent by weight of said preparation apart from said analgesic, which preparation is obtainable by extrusion of a melt comprising the constituents i) and
   ii) and subsequent shaping.

7. The preparation of claim 6, further comprising up to 30% by weight of a water-soluble saccharide or a sugar alcohol or a mixture thereof.

8. The preparation of claim 6, further comprising up to 20% by weight of one or more physiologically acceptable salts of sodium or of potassium.

9. The preparation of claim 6, further comprising up to 30% by weight of a water-soluble saccharide or a sugar alcohol or a mixture thereof, and up to 20% by weight of one or more physiologically acceptable salts of sodium or of potassium.

10. A transparent rapid release preparation an effective amount of a non-steroidal analgesic with antipyretic and antiinflammatory action, wherein the release of the analgesic measured by the USP XXII saddle method after 30 minutes is at least 70%, which is obtainable by extrusion of a melt essentially consisting of one or more non-steroidal analgesics with antipyretic and antiinflammatory action, and
    a) from 50 to 100% by weight of a homopolymer of N-vinylpyrrolidone having a Fikentscher K value of 30,
    b) from 0 to 30% by weight of a water-soluble saccharide or sugar alcohol, or a mixture thereof, and
    c) from 0 to 20% by weight of one or more physiologically acceptable salts of sodium or of potassium,
where the weight percentages are based on the total of a), b) and c), and subsequent shaping.

11. The preparation defined in claim 10, wherein the amount of component c) is from 5 to 20% by weight.

12. The preparation of claim 10 wherein the amount of component a) is from 80 to 95% by weight, and the amount of component c) is from 5 to 20% by weight, where the weight percentages are based on the total of a) and c).

13. The preparation defined in claim 10, wherein the non-steroidal analgesic is ibuprofen.

14. The preparation defined in claim 10, wherein component c) is sodium acetate.

* * * * *